US007683039B2

(12) United States Patent
Hung et al.

(10) Patent No.: US 7,683,039 B2
(45) Date of Patent: Mar. 23, 2010

(54) WATER SOLUBLE, RANDOMLY SUBSTITUTED PARTIAL N-, PARTIAL O-ACETYLATED CHITOSAN, PRESERVING COMPOSITIONS CONTAINING CHITOSAN, AND PROCESSES FOR MAKING THEREOF

(75) Inventors: William M. Hung, Alpharetta, GA (US); Katrina L. Bergbauer, Decatur, GA (US); Kai C. Su, Alpharetta, GA (US); Guigui Wang, Cumming, GA (US)

(73) Assignee: Adjuvant Pharmaceuticals, LLC, Alpharetta, GA (US)

( * ) Notice: Subject to any disclaimer, the term of this patent is extended or adjusted under 35 U.S.C. 154(b) by 263 days.

(21) Appl. No.: 10/746,085

(22) Filed: Dec. 24, 2003

(65) Prior Publication Data

US 2004/0127461 A1 Jul. 1, 2004

Related U.S. Application Data

(60) Division of application No. 10/045,959, filed on Oct. 19, 2001, now Pat. No. 6,716,970, which is a continuation-in-part of application No. 09/838,528, filed on Apr. 19, 2001, now abandoned, which is a continuation-in-part of application No. 09/611,160, filed on Jul. 6, 2000, now abandoned.

(60) Provisional application No. 60/199,406, filed on Apr. 21, 2000, provisional application No. 60/202,548, filed on May 10, 2000.

(51) Int. Cl.
*A61K 31/765* (2006.01)
*A61K 31/785* (2006.01)
*C08B 37/08* (2006.01)

(52) U.S. Cl. .................. 514/55; 424/78.04; 536/20
(58) Field of Classification Search .............. 424/78.04; 514/55; 536/20
See application file for complete search history.

(56) References Cited

U.S. PATENT DOCUMENTS

| 4,136,173 A * | 1/1979 | Pramoda et al. .......... 514/15 |
| 4,168,112 A | 9/1979 | Ellis et al. |
| 4,259,202 A | 3/1981 | Tanaka et al. |
| 4,826,826 A | 5/1989 | Conti |
| 4,885,168 A | 12/1989 | Hashimoto et al. |
| 4,909,942 A | 3/1990 | Sato et al. |
| 4,979,959 A | 12/1990 | Guire |
| 4,996,307 A | 2/1991 | Itoi et al. |
| 5,057,542 A | 10/1991 | Leuba et al. |
| 5,169,535 A | 12/1992 | Adachi et al. |
| 5,290,813 A | 3/1994 | Clark et al. |
| 5,409,731 A | 4/1995 | Nakagawa et al. |
| 5,422,116 A | 6/1995 | Yen et al. |
| 5,451,237 A | 9/1995 | Vehige |
| 5,520,920 A | 5/1996 | Castillo et al. |
| 5,536,155 A | 7/1996 | Futaki et al. |
| 5,549,919 A | 8/1996 | Ueno et al. |
| 5,589,591 A | 12/1996 | Lewis |
| 5,658,915 A | 8/1997 | Abe et al. |
| 5,770,628 A * | 6/1998 | Cantoro ..................... 514/778 |
| 5,891,913 A | 4/1999 | Sallmann et al. |
| 6,284,749 B1 | 9/2001 | Castillo et al. |
| 6,589,999 B2 | 7/2003 | Gurny et al. |

FOREIGN PATENT DOCUMENTS

| CN | 1229071 | 9/1999 |
| DE | 19826953 | * 11/1999 |
| DE | 19857548 | 8/2000 |
| JP | 63169975 A | 8/1988 |
| JP | 1010970 A | 1/1989 |
| JP | 1050014 A | 2/1989 |
| JP | 1265224 A | 10/1989 |
| JP | 1293314 A | 11/1989 |
| JP | 3102313 A | 4/1991 |
| JP | 5142502 | 6/1993 |
| JP | 6181970 | 7/1994 |
| JP | 7223966 A | 8/1995 |
| JP | 7324014 | 12/1995 |
| WO | WO 94/13774 | 6/1994 |
| WO | WO 96/20730 | 7/1996 |
| WO | WO 97/06782 | 2/1997 |
| WO | WO97/06782 | * 2/1997 |
| WO | WO 99/40790 | 8/1999 |
| WO | WO 00/30609 | 6/2000 |
| WO | WO 02/09513 A2 | 2/2002 |

OTHER PUBLICATIONS 2006-2007 Sigma Chemical Catalog, published 2006 by Sigma, pp. 482 and 2185.*
Machine translation of DE19826953, Reference cited above under Foreign Patent Documents.*
U.S. Appl. No. 07/986,959, Powell et al., "Compositions and Methods for Inhibiting and Reducing Lysozyme Deposition on Hydrophilic Contact Lenses," 27 pgs. (Filed: Dec. 9, 1992).

(Continued)

*Primary Examiner*—Shaojia Anna Jiang
*Assistant Examiner*—Eric S Olson
(74) *Attorney, Agent, or Firm*—Collen A. Beard

(57) ABSTRACT

The present invention is directed to a water soluble, randomly substituted partial N-, partial O-acetylated chitosans or chitosan derivatives and methods of preparing water soluble, randomly substituted partial N-, partial O-acetylated chitosans or chitosan derivatives comprising the steps of dissolving the chitosan or chitosan derivative into an aqueous acidic solution and reacting the chitosan or chitosan derivative with an acetylating agent in the presence of a phase transfer reagent. The present invention is further directed to a pharmaceutical preserving composition comprising: (a) at least one chitosan or chitosan derivative and (b) at least one buffer solution, as well as methods of preserving contact lens solutions and disinfecting contact lens using such composition.

17 Claims, No Drawings

OTHER PUBLICATIONS

Bough, W. et al., "Influence of Manufacturing Variables on the Characteristics and Effectiveness of Chitosan Products. II. Coagulation of Activated Sludge Suspensions," *Biotechnology and Bioengineering*, vol. XX, No. 12, pp. 1945-1955 (Dec. 1978).

Davydova, V. et al., "Interaction of Bacterial Endotoxins with Chitosan. Effect of Endotoxin Structure, Chitosan Molecular Mass, and Ionic Strength of the Solution on the Formation of the Complex," *Biochemistry*, vol. 65, No. 9, pp. 1082-1090 (2000).

Felt, O. et al., "Topical use of chitosan in ophthalmology: tolerance assessment and evaluation of precorneal retention," *International Journal of Pharmaceutics*, vol. 180, pp. 185-193 (1999).

Felt, O. et al, "Chitosan as Tear Substitute: A Wetting Agent Endowed with Antimicrobial Efficacy," *Journal of Ocular Pharmacology And Therapeutics*, vol. 16, No. 3, pp. 261-270 (2000).

Felt, O. et al., "Delivery of Antibiotics to the Eye Using a Positively Charged Polysaccharide as Vehicle," *AAPS Pharmaceutical*, http://www.pharmsci.org/scientificjournals/pharmsci/journal/01_34.html, Article 34, 9 pgs. (2001).

Hirano, S. et al., "Selective N-acylation of chitosan," *Carbohydrate Research*, vol. 47, pp. 315-320 (1976).

Kristiansen, A. et al., "The interactions between highly de-N-acetylated chitosans and lysozyme from chicken egg white studied by $^1$H-NMR spectroscopy," *Eur. J. Biochem.*, vol. 251, pp. 335-342 (1997).

Kristiansen, A. et al., "Competitive binding of highly de-N-acetylated chitosans and N,N'-diacetylchitobiose to lysozyme from chicken egg white studied by $_1$H NMR spectroscopy," *Carbohydrate Research*, vol. 289, pp. 143-150 (1996).

Kurita, K. et al., "Studies on Chitin, 3), Preparation of Pure Chitin, Poly(N-acetyl-D-glucosamine), from the Water-Soluble Chitin," *Makromol. Chem.*, vol. 178, pp. 2595-2602 (1977).

Kurita, K. et al., "Solubilization of a Rigid Polysaccharide: Controlled Partial N-Acetylation of Chitosan to Develop Solubility," *Carbohydrate Polymers*, vol. 16, pp. 83-92 (1991).

LeHoux, J. et al., "Some Effects of Chitosan on Liver Function in the Rat," *Endocrinology*, vol. 132, No. 3, pp. 1078-1084 (1993).

Sannan, T. et al., "Studies on Chitin, 2), Effect of Deacetylation on Solubility," *Makromol. Chem.*, vol. 177, pp. 3589-3600 (1976).

Schorigin, P. et al., "Über die Acetylierung des Chitins (Vorläufig. Mitteil.).," *Aus. d. Organ. Laborat. d. Wissenschaftl.* Instituts für Kunstseide, Moskau, 3 pgs. (1935).

Wu, A. et al., "Influence of Manufacturing Variables on the Characteristics and Effectiveness of Chitosan Products. III. Coagulation of Cheese Whey Solids," *Biotechnology and Bioengineering*, vol. XX, No. 12, pp. 1957-1966 (Dec. 1978).

\* cited by examiner

WATER SOLUBLE, RANDOMLY SUBSTITUTED PARTIAL N-, PARTIAL O-ACETYLATED CHITOSAN, PRESERVING COMPOSITIONS CONTAINING CHITOSAN, AND PROCESSES FOR MAKING THEREOF

CROSS REFERENCE TO RELATED APPLICATION

This application is a divisional application of U.S. application Ser. No. 10/045,959 filed on Oct. 19, 2001, now U.S. Pat. No. 6,716,970, which is a Continuation-In-Part of U.S. application Ser. No. 09/838,528 filed Apr. 19, 2001, now abandoned, which is a Continuation-In-Part of U.S. application Ser. No. 09/611,160 filed Jul. 6, 2000, now abandoned, which claims priority to U.S. Provisional Application Ser. Nos. 60/199,406, filed Apr. 21, 2000, and 60/202,548, filed May 10, 2000, which are all herein incorporated by reference in their entireties.

FIELD OF THE INVENTION

The present invention relates to novel water soluble, randomly substituted partial N-, partial O-acetylated chitosan or derivatives thereof, and preserving compositions containing water soluble, randomly substituted partial N-, partial O-acetylated chitosan, chitosan or derivatives thereof and novel processes for making water-soluble randomly substituted partial N-, partial O-acetylated chitosan, chitosan or derivatives thereof.

BACKGROUND OF THE INVENTION

Ophthalmic products intended for repeated use after opening, that is "multi-dose" products, must be preserved to minimize contamination with microorganisms during use. Preservatives that are used in ophthalmic solutions are often irritating to the eye, and at worst, may damage eye tissue after repeated use. Preservative problems may be worsened in contact lens solutions when a contact lens that has been exposed to a preservative in a lens care solution acts as a reservoir that concentrates the preservative in the eye.

In the United States, acceptably preserved pharmaceutical products, including ophthalmic, nasal and otic preparations, must achieve minimum performance standards when tested according to the procedures of the United States Pharmacopoeia Preservative Efficacy Test (PET). According to the PET protocol, adequately preserved formulations must): a) reduce 0 day challenge inocula of the bacteria *Staphylococcus aureus, Pseudomonas aeruginosa* and *Escherichia coli* by at least 99.9% (3 logs) within 14 days after the challenge date; b) prevent growth of *Aspergillus niger* and *Candida albicans* within 14 days following the 0 day challenge; and c) prevent growth of the test microorganisms beyond the 14 day levels up to day 28. To demonstrate preservative efficacy for contact lens care products, a modified PET procedure is required by the FDA wherein a re-challenge of the test solutions is done on day 14 after the 14 day organism concentrations are determined.

Chitosan, the de-acetylation product of chitin, is a non-toxic biopolymer with weak antimicrobial activity. Heretofore, the use of chitosan to preserve pharmaceutical compositions has been hampered by its insolubility at pH above 6 and also because the antimicrobial activity of Chitosan in acidic solutions, by itself, is too low to meet PET requirements. Chitosan's water solubility at near neutral pH can be improved by derivatization with hydrophilic functional groups, such as carboxymethyl or glycol substituents, or by selective N-acetylation of commercially available chitosans.

Considerable efforts have been made to extend the water solubility of chitosan at neutral pH. In Sannan et al., Makromol Chem. 177, 3589 (1976), it was reported that, by treatment of chitin with alkali under homogeneous conditions, chitin with about 50% deacetylation became water-soluble. However, long reaction time and large quantities of solvent are required in some stages, including neutralization of the reaction mixture and removal of the resulting salt. This laborious process would be troublesome especially in large-scale production.

Kurita et al., Carbohydrate Polymers 16, 83 (1991), also discloses preparing water-soluble chitosan with about 50% N-acetylation by acetylating a 90% deacetylated chitosan with a complex solvent system, comprising aqueous acetic acid/methanol/pyridine. Kurita et al. describes that the resultant partially N-acetylated chitosan is water soluble, if the degree of acetylation is controlled at 50% and the acetyl groups are distributed randomly. However, the huge excess of pyridine solvent used by the Kurita method made this process impractical. Furthermore, the reaction products have limited water solubility at neutral pH because heterogeneous reaction conditions were employed that restrict uniform, random acetylation. Specifically, Kurita's chitosan reactant was not soluble in the reaction mixture, but instead it was dispersed as a swollen gel which hindered complete availability of reaction sites. In this case, the acetylation reaction would be favored in those chain segments that were most exposed and free to the reaction mixture, while other parts of the gel would be comparatively less acetylated due to steric interference from adjacent polymer chain segments. When taken as a whole, the polymer chain is not uniformly random, but instead is comprised of blocks of higher and lower acetylation.

Kubota et al., Polymer Journal. 29, 123 (1997), reported to have a facile preparation of water-soluble N-acetylated chitosan. In this reference, the chitosan is degraded by treatment with $NaBO_3$, and the depolymerized product is then N-acetylated with acetic anhydride in aqueous acetic acid. Since both physical-chemical and biological properties of chitosan are dependent upon the chemistry of the polymer, such as the random distribution of a definite amount of acetyl groups and the molecular weight of the polymer, this process, which involves depolymerization, might alter the biological properties of chitosan.

SUMMARY OF INVENTION

The present invention is directed to a pharmaceutical preserving composition comprising: (a) at least one chitosan or chitosan derivative, and (b) at least one buffer solution.

The present invention is further directed to a method of preserving a contact lens solution, comprising mixing a contact lens solution with the composition comprising: (a) at least one chitosan or chitosan derivative, and (b) at least one buffer.

Moreover, the present invention relates to a method of disinfecting a contact lens, comprising soaking the contact lens with the composition comprising: (a) at least one chitosan or chitosan derivative, and (b) at least one buffer solution for a suitable period of time.

The present invention also is directed to a composition comprising (a) at least one chitosan or chitosan derivative, and (b) at least one buffer solution, wherein the at least one chitosan or chitosan derivative is prepared by a method comprising the steps of dissolving the at least one chitosan or chitosan derivative into an aqueous acidic solution and reacting the chitosan with an acetylating agent in the presence of a phase transfer reagent.

The present invention is further directed to a process for producing a water soluble, randomly substituted partial N-, partial O-acetylated chitosan or chitosan derivative, comprising the steps of dissolving a chitosan or chitosan derivative in an aqueous acidic solution and reacting the chitosan or chitosan derivative with an acetylating agent in the presence of a phase transfer reagent. In a further aspect, the invention relates to the product made by such a process.

The present invention is further directed to a water soluble, randomly substituted partial N-, partial O-acetylated chitosan or derivative thereof represented by the formula (I),

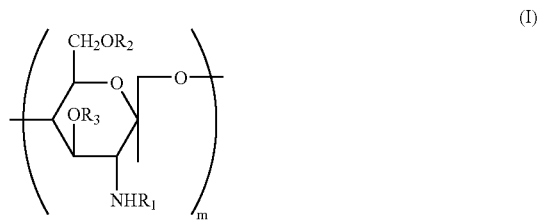

wherein $R_1$, $R_2$ and $R_3$ are independently H or $C(O)CH_3$, wherein the chitosan or derivative thereof is partially acetylated such that $R_1$ has a degree of substitution of $C(O)CH_3$ of from about 24 to about 55%, and $R_2$ has a degree of substitution of $C(O)CH_3$ of from about 1 to about 60%, m is greater than 25, wherein the partial N-, partial O-acetylated chitosan or derivative thereof is randomly substituted and is water soluble.

In another aspect, the invention provides a pharmaceutical preserving composition comprising:
 (a) at least one water soluble, randomly substituted partially N-, partial O-acetylated chitosan or derivative, of formula (I),
 (b) and at least one buffer solution.

In yet another aspect, the invention provides a pharmaceutical preserving composition comprising the product formed from mixing components (a) and (b) as described in the above aspect.

In another aspect, the invention provides a pharmaceutical preserving composition comprising:
 (a) at least one water soluble, randomly substituted partial N-, partial O-acetylated chitosan or derivative,
 (b) and at least one buffer solution,
wherein the at least one water soluble, randomly substituted partial N-, partial O-acetylated chitosan or chitosan derivative is prepared by a method comprising the step of reacting at least one randomly substituted partial N-, partial O-acetylated chitosan or chitosan derivative with a base in a solvent.

In another aspect, the invention provides a contact lens solution comprising the pharmaceutical preserving composition as described above.

In another aspect, the invention provides a contact lens solution comprising the product formed from mixing components (a) and (b) as described above.

In another aspect, the invention provides a process for producing a water soluble, randomly substituted partial N-, partial O-acetylated chitosan or chitosan derivative, comprising the step of reacting a randomly substituted partial N-, partial O-acetylated chitosan or chitosan derivative with a base in a solvent.

In another aspect, the invention provides a product produced by the method of reacting a water soluble, randomly substituted partial N-, partial O-acetylated chitosan or chitosan derivative with a base in a solvent.

In other aspects, the invention provides for products made by the processes of the invention.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention may be understood more readily by reference to the following detailed description of preferred embodiments of the invention and the Examples included therein.

Before the present compounds, compositions, articles, devices, and/or methods are disclosed and described, it is to be understood that this invention is not limited to specific synthetic methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an acyl" includes mixtures of acyl groups, reference to "a halogen" includes mixtures of two or more such halogens, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Aqueous acidic solution" means an aqueous solution having a pH below 7.0.

By the term "effective amount" of a compound or property as provided herein is meant such amount as is capable of performing the function of the compound or property for which an effective amount is expressed. The exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual without causing any undesirable biological effects or interacting in a deleterious manner with any of the other components of the pharmaceutical composition in which it is contained.

The term "water soluble" as used herein to describe the water soluble chitosans of the present invention, is meant to include chitosans or derivatives thereof having a water solubility of at least about 0.2% where solubility is measured by the test described for Examples 8-28 of the specification. Using this method, the water solubility of the randomly substituted partial N-, partial O-acetylated chitosan of the present invention is in one aspect at least 0.2%, in other aspects is up to 2%, and in other aspects (if greater than 0.200 g of chitosan is used in the test) is higher than 2%. Water solubilities of the chitosans of the present invention may be even higher than 2% or less than 0.2% when measured by other test methods. In such cases, the water solubility is dependent on the molecular weight of the polymer, the viscosity of the resulting aqueous chitosan solution and the conditions of the solubility test chosen.

By the term "randomly substituted" is meant a random substitution of acetyl groups on the chitosan main chain, which contributes to the water solubility or hydrophilicity of the resultant chitosan polymer.

By the term water soluble, "partial N-, partial O-acetylated chitosan" or derivative thereof is meant a poly(N-, O-acetylated-D-glucosamine).

By the term "degree of deacetylation" is meant the percentage of free amino groups on the water soluble, chitosan or chitosan derivative. The percent of N-acetylation can be calculated from the deacetylation value. The terms N-acetylation or O-acetylation are also referred to as the degree of substitution with $C(O)CH_3$ on either N or O.

It is to be understood that greater than 50% N-acetylation is sometimes described in the art as a chitin. However, the term "chitosan" is used throughout the invention herein to include chitosans and, if the N-acetylation is greater than 50%, to include chitins.

By the term "heterogeneous conditions" is meant that all or part of the reaction is carried out in a solid or highly swollen state, i.e., gel.

By the term "homogenous conditions" is meant that the reaction is carried out completely in a solution.

The present invention is a preserving composition for pharmaceutical products. The preserving composition can be used in various ophthalmic products such as contact lens rinsing, lubricating, cleaning and storage solutions, artificial tear solutions and ophthalmic drugs. The compositions of the instant invention may also be used to preserve otic and nasal solutions.

Contact lens solutions in particular present a special preservative challenge because lens wearers are usually exposed to the preserving agents for many years on a daily basis. The possibility that the lens wearer can experience discomfort or develop sensitivity to the preservative is even higher than would be the case in short-term exposure. Typical contact lens solution preserving agents used in the prior art are sorbic acid, thimerosal, or DYMED™(polyaminopropyl biguanide).

The composition of this invention comprises at least one chitosan or chitosan derivative, and at least one buffer solution. The composition of this invention additionally may contain at least one biocidal adjuvant. Compositions of the present invention contain these components in amounts to be effective as pharmaceutical preserving compositions useful for preserving pharmaceutical products, including ophthalmic, nasal and otic preparations.

One preferred embodiment is used as a contact lens solution preservative. Another preferred embodiment is used as a contact lens disinfection regimen. When the composition comprised of at least one chitosan or chitosan derivative and at least one buffer solution is used in a method to preserve a contact lens solution, the contact lens solution is mixed with the composition. When the composition comprised of at least one chitosan or chitosan derivative and at least one buffer solution is used in a contact lens disinfection regimen, the contact lens is rinsed and rubbed with the composition, and the contact lens then soaks in the composition for a suitable period of time, such as not less than 15 minutes, more preferably for not less than 1 hour, even more preferably not less than four hours. Preferably, the soaking occurs at room temperature; however, any suitable temperature may be employed.

In a preferred embodiment, the chitosan and chitosan derivatives of the present invention have the additional advantage of being capable of performing several functions normally requiring other ingredients. For instance, in a preferred embodiment, the chitosan or chitosan derivative may, in addition to its preserving role, act as a natural surfactant, and aid in lens cleaning by emulsifying lens proteins and lipids away from the lens surface into solution. Furthermore, chitosan, as a polymeric saccharide, can be used in a preferred embodiment as a solution thickening agent and lens lubricant thereby enhancing lens comfort by reducing lens drying rate. As such, the chitosan or chitosan derivative in one embodiment of this invention has a demulcent effect so as to enhance lens wearer comfort.

Example chitosan or chitosan derivatives include chitosan salts, water-soluble chitosan, water-soluble, randomly substituted partial N-, partial O-acetylated chitosan, chitosan oligosaccharide, carboxymethyl chitosan, and hydroxyalkyl chitosan. The hydroxyalkyl substituents of the hydroxyalkyl, chitosans and the carboxymethyl substituents of the carboxymethyl chitosans could be attached to any of the pendant nitrogen or oxygen groups on the chitin or chitosan ring subunit. Specific preferred hydroxyalkyl chitosans include but are not limited to, hydroxyethyl chitosan (also known as glycol chitosan), hydroxypropyl chitosan, dihydroxypropyl chitosan, hydroxybutyl chitosan and dihydroxybutyl chitosan.

Example water soluble, randomly substituted partial N-, partial O-acetylated chitosan derivatives include such salt thereof, oligosaccharide thereof, carboxymethyl chitosan thereof, and hydroxyalkyl chitosan thereof. The hydroxyalkyl substituents of such hydroxyalkyl chitosans and the carboxymethyl substituents of such carboxymethyl chitosans could be attached to any of the pendant nitrogen or oxygen groups on the chitin or chitosan ring subunit. Specific preferred hydroxyalkyl chitosans of the partial N-, partial O-acetylated chitosan, include but are not limited to, hydroxyethyl chitosan (also known as glycol chitosan), hydroxypropyl chitosan, dihydroxypropyl chitosan, hydroxybutyl chitosan and dihydroxybutyl chitosan.

In an embodiment, a water soluble, randomly substituted partial N-, partial O-acetylated chitosan or derivative thereof represented by the following formula (I)

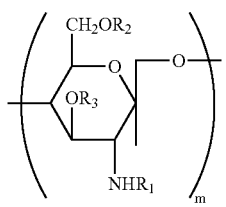

(I)

wherein $R_1$, $R_2$ and $R_3$ are independently H or $C(O)CH_3$, wherein the chitosan or derivative thereof is partially acetylated such that $R_1$ has a degree of substitution of $C(O)CH_3$ of from about 24 to about 55%, and $R_2$ has a degree of substitution of $C(O)CH_3$ of from about 1 to about 60%, m is greater than 25, wherein the partial N-, partial O-acetylated chitosan or derivative thereof is randomly substituted and is water soluble.

The term "m" is the number of repeat units in the water soluble, chitosan or polymer chain. In one aspect the molecular weight is about 100,000, but in other aspects the molecular weight can be higher. The molecular weight range of the water soluble chitosan or polymer chain herein refers to the weight average molecular weight. The weight average molecular weight of the water soluble chitosan or polymer is typically at least about 5,000. In one aspect the weight average molecular weight can be up to about 3,000,000, but in other aspects can be higher.

It is a separately surprising finding of one embodiment of this invention that chitosan or chitosan derivatives with certain buffer solutions such as borate or phosphate buffers, have higher antimicrobial activity as compared, for example, to similar formulations in citrate, and tromethamine (tris) buffers and in water. Thus, in one embodiment, the buffer solution may be comprised of a borate buffer. Suitable borate buffers include, but are not limited to, boric acid, sodium borate, potassium tetraborate, potassium metaborate, and mixtures of the same. In another embodiment, the buffer solution may be comprised of a phosphate buffer. Suitable phosphate buffers include, but are not limited to sodium dihydrogen phosphate and disodium hydrogen phosphate, and mixtures of the same.

The present invention includes a biocidal adjuvant. The biocidal adjuvant may be used against, for example, bacteria, fungi, and viruses. One advantage of the present invention is the surprising synergistic preservative effect of the composition. Suitable biocidal adjuvants include, but are not limited to, disodium ethylenediaminetetracetic acid (EDTA), nitrilotriacetic acid, and ethyleneglycol-bis(β-amino-ethylether)-N,N,N', N'-tetraacetic acid.

The present composition may contain several ingredients to perform the intended function of the composition. One possible additional component may be used to allow the composition to have an osmotic pressure near that of normal lachrymal fluids. Such a function may be achieved, for instance, by a tonicity agent, such as sodium chloride, potassium chloride or glycerol.

One feature of a preferred contact lens solution embodiment of the present invention is that proteins are stabilized against denaturing as compared to commercial multi-purpose contact lens solutions. In one embodiment, this effect may be accomplished by adding at least one surfactant to the composition. The surfactant may also aid in the cleaning of the lens.

Typical surfactants include, but are not limited to, Pluronics® or poloxamers, which are block copolymers of ethylene oxide and propylene oxide, or Tetronics® or poloxamine, which are block copolymers resulting from addition of ethylene oxide and propylene oxide to ethylene diamine. Other surfactants that may be used in the invention include, but are not limited to, tyloxapol, octoxynols, nonoxynols, and Tweens® or polyoxyethylene sorbitan fatty acid esters.

The contact lens solutions of the present invention may, in another embodiment, contain viscosity agents to provide lubrication to the eye. Typical viscosity agents include polymeric saccharides such as dextran, cellulose derivatives such as carboxymethyl cellulose and hydroxypropyl methylcellulose, polyvinyl alcohol, polyvinylpyrrolidinone, polyethylene glycol, and glycerin.

The present compositions have at least minimal preserving activity. In one embodiment, the biocidal activity of the composition is sufficient to meet the performance criteria of the Preservative Efficacy Test ("PET") of the USP (United States Pharmacopoeia) as modified by the FDA. As such, the present compositions reduce 0 day challenge inocula and 14 day re-challenge inocula of the bacteria *Staphylococcus aureus* (ATCC No. 6538), *Pseudomonas aeruginosa* (ATCC No. 9027) and *Escherichia coli* (ATCC No. 8739) by at least 99.9% (3 logs) within 14 days after the challenge and re-challenge dates, each. In the fungal challenge portion of the PET, the present composition does not allow any growth of *Aspergillus niger* (ATCC No. 16404) and *Candida albicans* (ATCC No. 10231) within 14 days following a 0 day challenge and a 14 day re-challenge. As such, the present invention may be used in a method of preserving a contact lens solution, wherein the contact lens solution is mixed with the composition.

In one embodiment, the composition of the present invention has a near neutral pH. This pH condition is preferred for compatibility with the organism, such as the human eye. As such, one preferred pH of the invention is from 6 to 8, preferably 6.6 to 7.8, and more preferably 6.8 to 7.2. Insofar as the antimicrobial activity alone of the composition is concerned, the lowest pH in the specified range is preferred. Given such preferred pH ranges, in one preferred embodiment, the chitosan or chitosan derivatives of the present invention are soluble at pharmaceutically acceptable pH levels. Another embodiment includes chitosan or chitosan derivatives that are near neutral soluble, meaning water soluble, from pH 6 to 8.

The chitosan and chitosan derivatives described in the present invention may be prepared by any method recognized in the art. Alternatively, in one preferred method, which is a method of one embodiment of the present invention, water-soluble, randomly substituted partial N-, partial O-acetylated chitosan and chitosan or chitosan derivative is prepared by dissolving the chitosan or chitosan derivative in an aqueous acidic solution and reacting the chitosan with an acetylating agent in the presence of at least one phase transfer reagent. The preparation of the water soluble, randomly substituted partial N-, partial O-acetylated chitosan or chitosan derivative thereof is carried out in a homogenous solution, which provides for the random acetylated substitution. The acetylating agent and phase transfer reagent(s) employed are used in an effective amount to be suitable for preparing the water-soluble, randomly substituted partial N-, partial O-acetylated chitosan and chitosan or chitosan derivative. In a preferred embodiment, the water soluble, randomly substituted partial N-, partial O-acetylated chitosan and chitosan preferably dissolves in solutions with near neutral pH values, such as from pH 6.0 to 8.0. Aqueous acidic solution refers to pH less than 7 and is typically the acidic pH used in the art for acetylation under heterogeneous conditions.

The acetylating agent acetylates the chitosan. As such, any known acetylating agent may be used. Example acetylating agents include, but are not limited to, acetyl halides, and acetic anhydride. A preferred acetylating agent is acetic anhydride.

The phase transfer reagent may be comprised of any phase transfer reagents known in the art. In general, the phase transfer reagent works across the water and organic phases. Suitable phase transfer reagents include, but are not limited to, those described in "Phase-Transfer Catalysis," Starks, C., et. al. Chapman & Hall, 1994, which is incorporated by reference in its entirety. Example phase transfer reagents include, but are not limited to, quaternary ammonium salts (Eq. I), quaternary phosphonium salts (Eq. II), crown ethers (Eq. IIIa-IIIc), and pyridinium salts (Eq. IV).

[A]w[B]x[C]y[D]zN+Q        (I)

or

[A]w[B]x[C]y[D]zP+Q−       (II)

where each of w, x, y and z is an integer from 0 to 4 and w+x+y+z=4

Q is a counter-ion selected from $F^-$, $Cl^-$, $Br^-$, $I^-$, $CH_3COO^-$, $OH^-$, $HSO_4^-$, $NO_3^-$, $PF_6^-$, $BF_4^-$, $HCOO^-$ and $H_2PO_4^-$; and A, B, C and D are each selected from $C_1$-$C_{18}$ alkyl, phenyl in which the phenyl ring is unsubstituted or substituted by $C_1$-$C_8$ alkyl, $C_1$-$C_8$ alkoxy, halo, hydroxy, phenoxy, nitro, carboxy, acetamido, or aryl, benzyl, cycloalkyl have 5-6 ring member or heterocyclic ring system.

In one preferred embodiment, quaternary ammonium salts (Eq. I) and quaternary phosphonium salts (II) include, but are not limited to, tetra $C_1$-$C_4$ alkyl ammonium halides, such as tetrabutylammonium bromide ("TBABr"), tetramethylammonium chloride ("TMACl"), tetrabutylammonium dihydrogen phosphate ("TBADHP"), and tetrabutyl ammonium iodide ("TBAI"); benzyl tri $C_1$-$C_4$ alkylammonium halides, such as benzyltriethylammonium chloride ("BTEACl"); and tetra $C_1$-$C_{18}$ phosphonium halides, such as tetrabutyl phosphonium bromide ("TBPBr") and hexadecyltributyl phosphonium bromide ("HDTRPBr").

A preferred embodiment includes a number of crown ethers (Eq. IIIa to IIIc) in practicing the present invention.

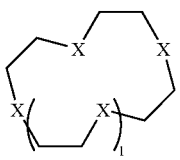

Eq. IIIa where

X=O or S, independently selected for each X l=1 to 3

In one preferred embodiment, suitable crown ethers according to Eq. IIIa include, but are not limited to, 12-crown-4, 15-crown-5, 18-crown-6 and 1,4,7,10,13,16-hexathiacyclooctadecane.

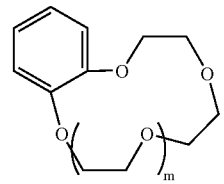

Eq. IIIb where m=1 to 3

In one preferred embodiment, suitable crown ethers in accordance with Eq. IIIb include, but are not limited to, benzo-12-crown-4, benzo-15-crown-5 and benzo-18-crown-6.

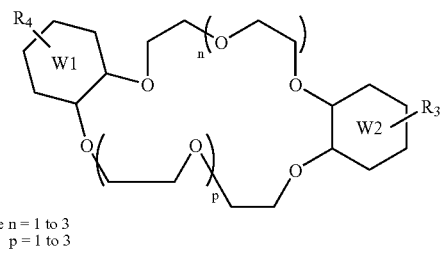

Eq. IIIc where n = 1 to 3
p = 1 to 3

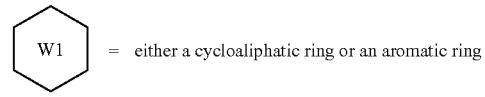
= either a cycloaliphatic ring or an aromatic ring

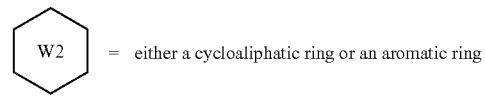
= either a cycloaliphatic ring or an aromatic ring $R_3$=H, $C_1$ to $C_4$ alkyl or halogen In one preferred embodiment, example crown ethers suitable for Eq. IIIc include, but are not limited to, dicylohexano-18-crown-6, dicyclohexano-24-crown-8, dibenzo-18-crown-6, dibenzo-21-crown-7, dibenzo-24-crown-8, dibenzo-30-crown-10, di-tere-butyl-di-benzo-18-crown-6 and '4-bromobenzo-18-crown-6.

Pyridinium salts (Eq. IV) may also be used in practicing the present invention.

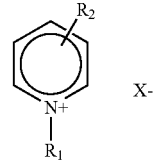

Eq. IV where $R_1$=$C_1$ to $C_{18}$ alkyl, benzyl or carboxymethyl
$R_2$=$C_1$ to $C_4$ alkyl, chloro, fluoro, bromo, hydroxy, $C_1$ to $C_4$ alkoxy or alkoxycarbonyl
X=counter ion of F, Cl, Br, I or p-toluene sulfonate.

Example pyridinium salts of Eq. IV include, but are not limited to, $C_1$ to $C_{18}$ alkyl pyridinium halides, such as 1-dodecylpyridinium chloride and 1-cetylpyridinium bromide, 1-benzyl pyridinium halides, and 1-benzyl-3-hydroxypyridinium chloride.

In another embodiment, which is a method of one embodiment of the present invention, the water-soluble chitosan or chitosan derivative is prepared by a method comprising the step of reacting at least one water soluble, randomly substituted partial N-, partial O-acetylated chitosan or chitosan derivative with a base in a solvent.

The base may be comprised of any bases known in the art. Example bases include, but are not limited to, alkaline hydroxides, such as potassium hydroxide or sodium hydroxide, and alkaline carbonates, such as sodium carbonate, or trisodium phosphate.

The solvent may be comprised of any solvent known in the art. Example solvents include, but are not limited to, alcohols, such as methanol, ethanol, or isopropanol, ethers such as diethyl ether or, tetrahydrofuran, polar solvents, such as dimethylformamide, dimethyl sulfoxide or, N-methyl pyrrolidinone and ketones such as acetone or 2-butanone.

This invention can be further illustrated by the following examples of various embodiments, although it should be understood that these examples are included merely for purposes of illustration and are not intended to limit the scope of the invention unless otherwise specifically indicated. The starting materials are commercially available unless otherwise described. All percentages are by weight unless otherwise described.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, percent is percent by weight, temperature is in ° C. or is at ambient temperature, and pressure is at or near atmospheric.

Example 1

Isotonic Aqueous Contact Lens Solution Containing Glycol Chitosan

| | |
|---|---|
| Glycol Chitosan | 0.25% |
| Pluronic F68 ™ (BASF Corporation) | 0.05% |
| Ethylenediaminetetraacetic acid, disodium salt dihydrate (EDTA) | 0.05% |
| Borate Buffer: | q.s. 100.00 mL |
| Sodium Borate Decahydrate | 0.08% |
| Boric Acid | 0.72% |
| Ultrapure Water | q.s. 100.00 mL |
| Sodium Hydroxide Solution (0.5M) | q.s.* pH = 6.9 |
| Sodium Chloride | q.s. Osmotic pressure = 300 mOsm |

*qs means quantum sufficit (as much as suffices), e.g. to bring the solution to volume This solution was prepared by dissolving glycol chitosan, Pluronic F68™ and EDTA in approximately 90% of the required volume of borate buffer. After all of the first components had dissolved, additional borate buffer was added to reach the desired volume. Sufficient volume of 0.5M sodium hydroxide solution was added to adjust the pH to 6.9. Sodium chloride was then added to adjust the osmotic pressure. The solution was sterilized by filtering through a 0.45 micron filter. The preserving efficacy of the solution was tested against the bacteria Staphylococcus aureus (ATCC No. 6538), Pseudomonas aeruginosa (ATCC No. 9027), Escherichia coli (ATCC No. 8739), and the fungi Aspergillus niger (ATCC No. 16404) and Candida albicans (ATCC No. 10231) according to the modified USP preservative efficacy test (PET) procedure described in the May, 1997 edition of Premarket Notification (510(k)) Guidance Document for Contact Lens Care Products (Developed by the U.S. Department of Health and Human Services, Food and Drug Administration, Center for Devices and Radiologic Health).

Following this procedure, the test solution was initially challenged with at least $10^5$ microorganisms/mL (cfu/mL) for each species tested, in duplicate, and at day 14, a re-challenge of the test solutions was done wherein the viable concentration of each organism type was adjusted to at least $10^4$ cfu/ml. The numbers of surviving microorganisms were determined at day 14, prior to the rechallenge inoculum adjustment, and at day 28. The test solution was deemed to be effectively preserved if viable bacteria were reduced at least 3 logs on days 14 and 28, and if viable fungi at days 14 and 28 were less than or equal to the challenge concentrations, (i.e. a log reduction of 0 or more). As shown below the results of the PET indicate that Example 1 is effectively preserved.

TABLE 1-a

Preservative efficacy test results for Example 1

| Microorganism | Average Organism Log Reduction | | Effectiveness[1] |
|---|---|---|---|
| | 14 days | 28 days | |
| Escherichia coli (Ec) | 3.6 | 3.7 | Pass |
| Pseudomonas aeruginosa (Pa) | 5.7 | 3.6 | Pass |
| Staphylococcus aureus (Sa) | 5.1 | 3.3 | Pass |
| Candida albicans (Ca) | 1.1 | 2 | Pass |
| Aspergillus niger (An) | 1.5 | 1 | Pass |

Note:
[1] At least 3 log reduction required for Ec, Pa and Sa at 14 and 28 days
At least 0 log reduction required for Ca and An at 14 and 28 days Denaturing of tear proteins on soft contact lenses is a common problem. Once proteins denature on the lens, they are difficult to remove, reduce lens clarity, may cause allergic reactions for the wearer, and can act as attachment sites for infectious microorganisms. Lysozyme, especially is a potentially troublesome tear protein insofar as high water (~55% water) contact lenses are concerned because lysozyme is a positively charged protein that is readily attracted to the negatively charged lens surface. An in vitro assay was developed to determine the ability of a test solution to retard lysozyme denaturing. In this assay, a 1% stock solution of lysozyme in isotonic borate buffered saline (pH=7.0) is freshly prepared, and an aliquot of this stock solution is mixed with an equal aliquot of a test solution. The resulting mixture is heated at 75° C. for 15 minutes in a hot water bath. After the mixture is removed from the heating bath, it is allowed to cool to room temperature before it is visually inspected for signs of protein denaturing as evidenced by the formation of a white precipitate.

Example #1 was evaluated using the described lysozyme assay in comparison to several commercial contact lens multi-purpose solutions, and the results from the assay represented in Table 1-b indicate that only Example #1 prevented lysozyme denaturing.

TABLE 1-b

Comparison of protein denaturation for Example 1
and commercial contact lens multi-purpose solutions

| Test Solution | Ingredients | Appearance after Lysozyme Assay (75° C., 15 min.) |
|---|---|---|
| COMPLETE ® Comfort Plus ™ (Allergan) | Phosphate Buffer, Potassium & Sodium Chloride, Edetate Disodium, Poloxamer 237, Hydroxypropyl methylcellulose, PHMB (1 ppm) | Precipitate |
| ReNu MultiPlus ® (Bausch & Lomb) | Borate Buffer, Sodium Chloride, Edetate Disodium, Poloxamine, Hydroxyalkylphosphonate, DYMED ™ (1 ppm) | Precipitate |
| Opti-Free ® Express ®(Alcon Laboratories, Inc.) | Citrate Buffer, Sodium Chloride, Edetate Disodium (0.05%), POLYQUAD ® (10 ppm) | Precipitate |
| Chlorhexidine Solution | Borate Buffer, Sodium Chloride, Chlorhexidine (50 ppm) | Precipitate |
| Chlorhexidine Diacetate Dihydrate | Borate Buffer, Sodium Chloride, Chlorhexidine diacetate dihydrate (50 ppm) | Precipitate |
| Borate Buffered Saline (Control) | Borate Buffer, Sodium Chloride | Hazy Solution Slight Precipitate |
| Example 1 | Borate Buffer, Sodium Chloride, Glycol Chitosan, Poloxamer 188, EDTA | Clear Solution No Precipitate |

Ocular irritation and in vitro biocompatibility was also evaluated for the Example 1 formulation. The degree of ocular irritation and epithelial cell layer staining was evaluated in 6 rabbits in accordance with methods proposed by Draize J H, Woodard G, and Calvery H O: Methods for the Substances Applied Topically to the Skin and Mucous Membranes. J. Pharmacol. Ext. Ther. (1944)82: 377-390. After a preliminary examination and Draize scoring of both eyes, each rabbit received eight (8) hourly 10 microliter instillations of Example 1 to the surface of the right eye only, with the left untreated eye serving as a control. Within 1 hour after the last application of test solution and again after 24, 48 and 72 hours, all eyes were evaluated in accordance with the Draize scoring method. Slit-lamp biomicroscopic examination using the McDonald-Shadduck scoring method (McDonald, T. O. and Shadduck J. A. 1977. Eye Irritation. Pages 162-166 in F. N. Marzulli and H. I. Maibach, eds. *Advances in Modern Toxicology*, Vol. 4, *Dermatotoxicology and Pharmacology*. Halsted Press, John Wiley & Sons, Inc., New York.) was also done at the end of the day of the solution instillations. The Draize and McDonald-Shadduck scoring for the test and control eyes for all rabbits were "0", meaning that Example 1 was non-irritating to the ocular surface of the rabbit eye.

The in vitro biocompatibility study of Example 1 was based on the agar diffusion test described in USP/NF 22 (87) Biological Reactivity Tests In-Vitro. In this evaluation, a filter disc with a 0.1 ml aliquot of Example 1, and appropriate negative and positive control discs were each placed on duplicate agarose surfaces directly overlaying confluent monolayers of L-929 mouse fibroblast cells. After incubating at 37 C in 5% $CO_2$ for 24-26 hours, the cultures were examined, revealing that Example 1 showed no evidence of causing cell lysis or toxicity, thus meeting the biocompatibility requirements of the USP (see table 1-c).

TABLE 1-c

In vitro biocompatibility evaluation results for Example 1

| Test/Control Articles[1] | Sample No. | Zone of Lysis (mm) | Grade[2] | Reactivity[1] |
|---|---|---|---|---|
| Example 1 | 1 | 0.0 | 0 | None |
| | 2 | 0.0 | 0 | None |
| Filter Disc Control | 1 | 0.0 | 0 | None |
| | 2 | 0.0 | 0 | None |
| Positive Control | 1 | 5.0 | 3 | Moderate |
| | 2 | 5.0 | 3 | Moderate |
| Negative Control | 1 | 0.0 | 0 | None |
| | 2 | 0.0 | 0 | None |

[1]Filter disc control: 0.1 ml 0.9% sodium chloride irrigation, USP applied to a paper filter disc; Positive control: tin stabilized polyvinyl chloride; Negative control: low density polyethylene.
[2]Grade 0, Reactivity None: No detectable zone around or under specimen
Grade 1, Reactivity Slight: Some malformed or degenerated cells under specimen
Grade 2, Reactivity Mild: Zone limited to area under specimen and up to 4 mm
Grade 3, Reactivity Moderate: Zone extends 5-10 mm beyond specimen
Grade 4, Reactivity Severe: Zone extends greater than 10 mm beyond specimen Example 2

This example illustrates the activity of different hydroxyalkyl chitosan solutions against *Escherichia coli* in a 28 day USP Preservative Efficacy Test (PET). Solutions 2a-e were prepared as described in Example 1, using the following recipe.

Example Formulations #2a-e 0.05% EDTA 1.00% Boric Acid

Ultrapure Water (q.s. adj 100.00 mL)

0.5M Sodium Hydroxide (q.s. adj pH=6.9)

Sodium Chloride (q.s. adj mOsm=300)

a: control; b=0.25% glycol chitosan (SIGMA Chemical); c=0.25% hydroxypropyl chitosan (Austin Chemical Co.); d=0.25% hydroxybutyl chitosan (Austin Chemical Co.); e=0.25% di-hydroxypropyl chitosan (Technology Resource International Corporation).

The conditions of the PET were the same as those for Example 1 except that a re-challenge inoculum was not introduced at day 14. For this test, E. coli only was chosen as the screening microorganism because earlier tests showed that it was typically more resistant than other PET bacteria to chitosan antimicrobial formulations. Thus, antimicrobial activity against E. coli was deemed predictive of efficacy against the other PET microorganisms.

Referring to Table 2, it can be seen that all of the test solutions met the requirements of the USP PET for E. coli, namely that the number of viable bacteria were reduced by at least 3 logs by day 14 following the initial bacterial challenge, and the concentrations of the test bacteria decreased from the 14 day levels during the remainder of the 28 day test period.

TABLE 2

Preservative efficacy of solutions 2a-2e against *Escherichia coli*

| Formulation | Average E. coli Log Reduction | | Effectiveness[1] |
|---|---|---|---|
| | 14 days | 28 days | |
| 2a (control) | 0.9 | 2.5 | Fail |
| 2b (glycol chitosan) | 4.2 | 4.7 | Pass |
| 2c (hydroxypropyl chitosan) | 3.9 | 4.3 | Pass |
| 2d (hydroxybutyl chitosan) | 4.3 | 4.8 | Pass |
| 2e (dihydroxypropyl chitosan) | 4.2 | 5.3 | Pass |

Note:
[1] At least 3 log reduction required at day 14 and at least 3 log reduction must be maintained through day 28.

Example 3

This example illustrates the effect of pH on the antimicrobial activity of glycol chitosan. The test organism that was evaluated in Example 3 is *Pseudomonas aeruginosa* (ATCC No. 9027), a microorganism that is a particular problem in a common contact lens associated eye infection, infectious keratitis.

Example 3 Formulations

| | |
|---|---|
| Glycol chitosan (Sigma Chemical) | 0.5% |
| Pluronic ™ F68 (BASF Corporation) | 0.05% |
| EDTA | 0.05% |
| Sodium borate decahydrate | 0.08% |
| Boric acid | 0.72% |
| Ultrapure Water | q.s. adj 100.00 mL |
| Sodium hydroxide solution (0.5M) | q.s. pH = 6.6, 7.2 or 7.8 |
| Sodium chloride | q.s. mOsm = 300 ± 10 |

TABLE 3

Comparison of the antimicrobial activity of Example 3 against *Pseudomonas aeruginosa* Cfu *Pseudomonas aeruginosa* after 24 hours[1,2]

| PH = 6.6 | pH = 7.2 | pH = 7.8 |
|---|---|---|
| 2 | 184 | >1000 |

Notes:
[1] Challenge inoculum was $10^6$ cfu/mL
[2] Data shown is from the $10^5$ cfu recovery plates The table above, shows the average number of surviving colonies on the $10^5$ recovery plates that were prepared 24 hours after challenging the test formulations with $10^6$ cfu/mL *Pseudomonas aeruginosa*. As can be seen from this data, the pH 6.6 and 7.2 formulations of glycol chitosan were more effective in killing *P. aeruginosa* in 24 hours than the glycol chitosan formulation at pH=7.8.

Example 4

This example illustrates the antimicrobial activity of a water-soluble, randomly substituted partial N-, partial O-acetylated chitosan formulation wherein the randomly substituted, water-soluble partial N-, partial O-acetylated chitosan was prepared according to the method disclosed in Example 10.

Example 4 was formulated as follows: 500 ppm of the water soluble, randomly substituted partial N-, partial O-acetylated chitosan was dissolved in borate buffer (from Example 1) and 250 ppm EDTA was added. 0.5M sodium hydroxide solution was used to adjust the pH of the solution to 7.0, the osmotic pressure of the solution was adjusted with sodium chloride to 300 mOsm, and the solution was sterile filtered through a 0.45 micron membrane.

The antimicrobial activity was determined for Example 4 at days 14 and 28 according to the methods of the FDA modified USP preservative efficacy test as described in Example 1. The results summarized in Table 4 show that Example 4 passed the requirements of the preservative efficacy test.

TABLE 4

Preservative efficacy test results for Example 4

| Microorganism | Average Organism Log Reduction After 14 and 28 days | | |
|---|---|---|---|
| Effectiveness[1] | Day 14 | Day 28 | |
| *Escherichia coli* (Ec) | 4.8 | 3.8 | Pass |
| *Pseudomonas aeruginosa* (Pa) | 4.4 | 4.2 | Pass |
| *Staphylococcus aureus* (Sa) | 3.7 | 3.0 | Pass |
| *Candida albicans* (Ca) | 1.2 | 0.8 | Pass |
| *Aspergillus niger* (An) | 0.9 | 0.9 | Pass |

[1] At least 3 log reduction required for Ec, Pa and Sa at 14 and 28 days
At least 0 log reduction (i.e. stasis) required for Ca and An at 14 and 28 days Example 5

Example 5 illustrates the effect of various buffers on the antimicrobial activity of a water-soluble, randomly substituted partial N-, partial O-acetylated chitosan formulation.

The water-soluble, randomly substituted partial N-, partial O-acetylated chitosan in Example 5 was prepared according to the method disclosed in Example 10.

Example 5

Isotonic aqueous contact lens solution containing water-soluble, randomly substituted partial N-, partial O-acetylated chitosan in borate, phosphate, tris and citrate buffers

|  | Concentration |
| --- | --- |
| Randomly Substituted, water-soluble partial N-, partial O-acetylated chitosan according to Example 10. | 0.10% |
| Ethylendiaminetetraacetic acid, disodium salt dihydrate (EDTA) | 0.05% |
| Buffer (borate, phosphate, tris or citrate)*: | q.s.** 100.00 mL |
| Sodium hydroxide solution (0.5M) | q.s.** pH = 6.9 |
| Sodium chloride | q.s.** Osmotic pressure = 300 mOsm |

Note:
*Borate buffer is the same as described in Example 1
Phosphate buffer contains 0.08% sodium dihydrogen phosphate and 0.48% Disodium hydrogen phosphate in water
Tris buffer contains 1% tris(hydroxymethyl)aminomethane hydrochloride in water
Citrate buffer contains 1.5% sodium citrate in water
**q.s. means quantum sufficit (a sufficient volume), i.e. to bring the solution to volume The four solutions listed above were prepared as described for Example 4. The antimicrobial activity against *E. coli* was determined for each solution at days 14 and 28 using the preservative efficacy test methods described in Example 1. The results of the antimicrobial activity test data in Table 5 reveal that the antimicrobial activity of the borate buffered solution was more than 2 logs higher on days 14 and 28 than that of the other solutions, and the activity of the phosphate buffered randomly substituted partial N-, partial O-acetylated chitosan was higher than the TRIS and citrate buffered randomly substituted partial N-, partial O-acetylated chitosans.

TABLE 5

Comparison of the antimicrobial activity against *E. coli* of water-soluble, randomly substituted partial N-, partial O-acetylated chitosan in borate, phosphate, tris and citrate buffers.

|  | Average Log Reduction *E. coli* | |
| --- | --- | --- |
| Example 5, Buffer Type | Day 14 | Day 28 |
| Borate | 5.2 | 5.7 |
| Phosphate | 2.4 | 2.9 |
| TRIS | 1.5 | 2.0 |
| Citrate | 2.0 | 0.9 |

Example 6

Example 6 illustrates the importance of EDTA in combination with randomly substituted partial N-, partial O-acetylated chitosan to achieve preservative efficacy against *Escherichia coli*.

The composition of solutions 6a-h is shown below.

| Ex. No. | Randomly substituted water-soluble partial N-, partial O-acetylated chitosan (ppm) | Poloxamer 188 (ppm) | EDTA (ppm) |
| --- | --- | --- | --- |
| 6-a | 1000 | 0 | 500 |
| 6-b | 0 | 0 | 500 |
| 6-c | 1000 | 0 | 0 |
| 6-d | 0 | 0 | 0 |
| 6-e | 1000 | 500 | 500 |
| 6-f | 0 | 500 | 500 |
| 6-g | 1000 | 500 | 0 |
| 6-h | 0 | 500 | 0 |

The water-soluble, randomly substituted partial N-, partial O-acetylated chitosan used in the above test solutions was prepared according to the method described in Example 10. The above-listed ingredients are dissolved in borate buffer as in Example 1. In addition the pH of each solution was adjusted to 7.0 with 0.5M sodium hydroxide solution and the osmolality of each solution was adjusted to 300 mOsmoles with sodium chloride.

The antimicrobial activity of the solutions 6a-h against *E. coli* was determined at days 14 and 28, according to the methods of the PET as described in Example 1, and the results are summarized in Table 6.

TABLE 6

Antimicrobial activity against *E. coli* for Examples 6a-h

|  | Average Log Reduction *E. coli* | | Preservative |
| --- | --- | --- | --- |
| Example No. | Day 14 | Day 28 | Effectiveness[1] |
| 6-a | 4.0 | 4.9 | Pass |
| 6-b | 1.9 | 1.7 | Fail |
| 6-c | 2.1 | 0.9 | Fail |
| 6-d | 0.6 | 0.6 | Fail |
| 6-e | 5.2 | 5.1 | Pass |
| 6-f | 1.9 | 1.9 | Fail |
| 6-g | 1.9 | 1.5 | Fail |
| 6-h | 0.6 | 0.5 | Fail |

[1] At least 3 log reduction required at 14 and 28 days to pass PET

As can be seen in table 6, only solutions 6-a and 6-e caused the minimum 3 log reduction on days 14 and 28 that is required to demonstrate preservative efficacy against *E. coli*. By comparison, the antimicrobial activity of the corresponding control solutions 6-b (for 6-a) and 6-f (for 6-e) in which randomly substituted partial N-, partial O-acetylated chitosan was removed, and the control solutions 6-c (for 6-a) and 6-g (for 6-e) in which EDTA was removed, was less than half that of the randomly substituted partial N-, partial O-acetylated chitosan/EDTA solutions. Thus, it appears from this data, that EDTA and randomly substituted partial N-, partial O-acetylated chitosan are acting synergistically to provide the unexpected result that higher antibacterial activity against *E. coli* is obtained with randomly substituted partial N-, partial O-acetylated chitosan and EDTA than with either ingredient formulated without the other.

TABLE 7

Preservative efficacy test results for chitosan oligosaccharide solutions

| | Average Organism Log Reduction after 14 and 28 days | | | | | | | | | | |
|---|---|---|---|---|---|---|---|---|---|---|---|
| | E. coli | | P. aeruginosa | | S. aureus | | C. albicans | | A. niger | | Passed |
| Test Solution | 14 d | 28 d | 14 d | 28 d | 14 d | 28 d | 14 d | 28 d | 14 d | 28 d | PET? |
| Oligo. Chitosan in Water[1] | 0.1 | +0.4 | +0.3 | +1.2 | 4.9 | 4.9 | 0.3 | 0.2 | 0.2 | 0.3 | No |
| Oligo. Chitosan in Water + EDTA[1,2] | 1.9 | 0.9 | +0.2 | 0.0 | 3.1 | 2.6 | 0.4 | 0.3 | 0.1 | +0.1 | No |
| Oligo. Chitosan in Borate Buffer + EDTA[1,2,3] | 5.8 | 4.8 | 5.9 | 4.0 | 4.4 | 4.2 | 4.3 | 3.7 | 1.3 | 0.2 | Yes |

[1] Contains 1000 ppm oligosaccharide chitosan (lot # COS-KL225, Kitto Life Co., LTD. Seoul Korea), pH adjusted to 7.0 with 0.5 M sodium hydroxide, osmolality adjusted to 300 mOsmoles with sodium chloride.
[2] Contains 250 ppm ethylenediaminetetraacetic acid, disodium salt dihydrate (EDTA).
[3] Borate buffer as described in Example 1.

Example 7

In this example the preservative effectiveness of solutions of chitosan oligosaccharide are evaluated wherein the comparative solutions include (1) water, (2) water with EDTA, and (3) borate buffer with EDTA. The pH and osmolality of the test solutions were adjusted to 7.0 and 300 mOsmoles, respectively, as described in Example 1, and the preservative test conditions are described in Example 1. It can be seen from the data shown in Table 7, that neither of the water solutions of chitosan oligosaccharide provided the 3 log reduction of P. aeruginosa and E. coli at day 14 and day 28 that is required to pass the modified USP preservative effectiveness test with re-challenge at day 14. In contrast, the oligosaccharide formulated in borate buffer was effectively preserved since it reduced the concentrations of all of the bacteria tested by more than 3 logs, and prevented the growth of the fungi, C. albicans and A. niger.

Solubility Test

In the following examples 8-28 and comparative samples A-C, a mixture of 0.200 g of a sample of chitosan in 10 ml of DI water was stirred at room temperature for approximately eighteen hours. The solution was filtered through #1 qualitative filter paper, and the container was washed with a small amount of deionized water. The combined filtrate was then placed in a weighed aluminum weighing dish and dried in an vacuum oven at around 60° C. The observed weight difference is the weight of soluble solid. The results are shown in Tables 8-11 as solubility in water (%), whereby 2% is the maximum measurable solubility attainable under the conditions of this test (based on 0.200 g of chitosan in 10 ml of water). Some water soluble chitosans of the present invention have an actual solubility greater than 2%. To determine if such actual solubility is greater than 2%, more than 0.200 g of chitosan must be used (for 10 ml water). Some water soluble, randomly substituted partial N, partial O-acetylated chitosans may have higher water solubility than 2% when evaluated according to the conditions of other solubility methods.

Two samples were prepared according to Kurita's process; however, both samples have rather poor solubility in water at neutral pH value.

Comparative Example A

Following the procedure described in Kurita et al., Carbohydrate Polymers 16, 83 (1991), method D, a solution of 3.0 g of chitosan with 84% deacetylation in 80 ml of 10% aqueous acetic acid was diluted with 80 ml of methanol and poured into 1000 ml pyridine to give a highly swollen precipitate. 7.7 g of acetic anhydride was added at room temperature and after stirring for five hours, the mixture was poured into 3 liters of acetone. The precipitate was collected by filtration, washed with acetone, and dried to obtain 3.31 g of solid. The degree of deacetylation value and O-acetylation value were determined by the $^1$HNMR method referenced in Example 8. (Although Kurita does not disclose NMR data, our NMR data of the Kurita product indicated the presence of both N-, and O-acetylation.)

Comparative Example B

Comparative example B was prepared by proceeding in a manner similar to that described in comparative example A, except 11.1 g of acetic anhydride was used. There was obtained 3.45 g of solid. The degree of deacetylation value and O-acetylation value were determined by the $^1$HNMR method referenced in Example 8.

Comparative Example C

Comparative example C was prepared according to the procedure described in example 4, except no tetrabutylammonium bromide was added. There was obtained 4.17 g of solid. The degree of deacetylation value and O-acetylation value were determined by the $^1$HNMR method referenced in Example 8.

Example 8

A viscous solution was prepared by dissolving 13.5 g of chitosan with deacetylation degree of 84% in 600 ml of 10% acetic acid solution. 1.35 g of benzyltriethylammonium chloride was added, followed by 38.5 g of acetic anhydride. The resulting mixture was stirred at room temperature for approximately eighteen hours. 400 ml of methanol was added and the mixture was stirred for an additional 30 minutes. The reaction mixture was then transferred into an additional funnel followed by the slow addition of 2400 ml of acetone with good agitation. The precipitate was collected and then washed with acetone until no detectable amount of acetic acid remained. The resultant solid weighed 12.24 g. The degree of deacetylation (DD) value and O-acetylation value were determined by $^1$H NMR method. (A. Hirai, H. Odani and A. Nakajima: Polymer Bulletin 26, 87 (1991)). DD refers to the percentage of N-deacetylation. The percentage of N-acetylation (degree of substitution with C(O)CH$_3$) is 100-DD.

Example 9

In a procedure similar to that described in example 8, 10.25 g of chitosan, 450 ml of 10% acetic acid, 2.56 g of tetrabutyl ammonium bromide and 26.05 g of acetic anhydride were reacted at room temperature for approximately eighteen hours to get 11.19 g of solid. The degree of deacetylation (DD) value and O-acetylation value were determined by the $^1$HNMR method referenced in example 8.

Example 10

Proceeding in a manner similar to that described in example 8, 13.5 g of chitosan, 600 ml of 10% acetic acid, 3.375 g of tetrabutylammonium bromide and 17.2 g of acetic anhydride were interacted to get 14.72 g of solid. The degree of deacetylation (DD) value and O-acetylation value were determined by the HNMR method referenced in example 8.

Example 11

Following the procedure described in example 8, 3.347 g of chitosan, 150 ml of 10% acetic acid, 0.335 g of tetrabutyl ammonium bromide and 5.725 g of acetic anhydride were interacted to get 3.14 g of solid. The degree of deacetylation (DD) value and O-acetylation value were determined by the $^1$HNMR method referenced in example 8.

Example 12

Example 12 was prepared by a procedure similar to that described in example 11, except tetrabutylammonium bromide was replaced by benzyltriethylammonium chloride. There was obtained 3.69 g of solid. The degree of deacetylation value and O-acetylation value were determined by the $^1$HNMR method referenced in example 8.

Example 13

Example 13 was prepared following the procedure described in example 11, except 9.54 g of acetic anhydride was used to obtain 4.04 g of solid. The degree of deacetylation (DD) value and O-acetylation value were determined by the $^1$HNMR method referenced in example 8.

Example 14

Example 14 was prepared following a procedure similar to that described in example 11, except tetrabutylammonium bromide was replaced by tetramethyl ammonium chloride. There was obtained 3.54 g of solid. The degree of deacetylation value and O-acetylation value were determined by the $^1$HNMR method referenced in Example 8.

Example 15

Example 15 was prepared according to the procedure described in example 11, except tetrabutylammonium bromide was replaced by tetrabutylammonium iodide. There was obtained 4.33 g of solid. The degree of deacetylation value and O-acetylation value were determined by the $^1$HNMR method referenced in example 8.

Example 16

Example 16 was prepared according to the procedure described in example 11, except tetrabutylammonium bromide was replaced with tetrabutylammonium dihydrogen phosphate. There was obtained 4.13 g of solid. The degree of deacetylation value and O-acetylation value were determined by the $^1$HNMR method referenced in Example 8.

TABLE 8

Effect of quaternary ammonium salts on the water solubility of randomly substituted partial N-, partial O-acetylated chitosan

| Samples | Catalyst | DD value (%) (by NMR) | O-acetylation (%) (by NMR) | Solubility in water (%) |
|---|---|---|---|---|
| Vanson chitosan | | 84 | 0 | 0.025 |
| Compare sample A | None | 63.5 | 16.9 | 0* |
| Compare sample B | None | 66.7 | 12.3 | 0.10# |
| Compare sample C | None | 55.6 | 21.3 | 0.015# |
| Example 8 | BTEACl(1:4)** | 54.4 | 19.4 | 1.87 |
| Example 9 | TBABr (1:4) | 57.9 | 18.0 | 2.00 |
| Example 10 | TBABr (1:4) | 74.1 | 17.3 | 1.83 |
| Example 11 | TBABr (1:10) | 64.3 | 16.8 | 1.93 |
| Example 12 | BTEACl (1:10) | 67.2 | 23.7 | 2.00 |
| Example 13 | TBABr (1:10) | 58 | 32.5 | 1.95 |
| Example 14 | TMACl (1:10) | 58.4 | 19.9 | 2.00 |
| Example 15 | TBAI (1:10) | 57.7 | 46.0 | 2.00 |
| Example 16 | TBADHP (1:10) | 59.8 | 48.8 | 1.89 |

*The highly viscous gel could not be filtered through #1 filter paper
Only small amount of highly viscous gel filtered through #1 filter paper
**weight of catalyst vs. weight of chitosan

Example 17

Example 17 was prepared by following the procedure described in example 8, by reacting 13.5 g of chitosan, 600 ml of 10% acetic acid, 1.35 g of hexadecyltributyl phosphonium bromide and 38.5 g of acetic anhydride at room temperature for approximately eighteen hours to get 13.61 g of solid. The degree of deacetylation value and O-acetylation value were determined by the $^1$HNMR method referenced in example 8.

Example 18

Proceeding in a manner similar to that described in example 8, 13.5 g of chitosan, 600 ml of 10% acetic acid, 1.35 g of tetrabutyl phosphonium bromide and 38.5 g of acetic anhydride were interacted to get 13.32 g of solid. The degree of deacetylation value and O-acetylation value were determined by the $^1$HNMR method referenced in example 8.

TABLE 9

Effect of quaternary phosphonium salts on the water solubility of randomly substituted partial N-, partial O-acetylated chitosan

| Sample | Catalyst | DD value (%) (by NMR) | O-acetylation (%) (by NMR) | Solubility in water (%) |
|---|---|---|---|---|
| Vanson chitosan | | 84 | 0 | 0.025 |
| Comparison sample A | None | 63.5 | 16.9 | 0* |
| Comparison sample B | None | 66.7 | 12.3 | 0.10# |
| Comparison sample C | None | 55.6 | 21.3 | 0.015# |
| Example 17 | HDTBPBr (1:10)** | 54.1 | 22.4 | 1.86 |

TABLE 9-continued

Effect of quaternary phosphonium salts on the water solubility of randomly substituted partial N-, partial O-acetylated chitosan

| Sample | Catalyst | DD value (%) (by NMR) | O-acetylation (%) (by NMR) | Solubility in water (%) |
|---|---|---|---|---|
| Example 18 | TBPBr (1:10) | 54.4 | 32.8 | 1.76 |

*The highly viscous gel could not be filtered through #1 filter paper
Only small amount of highly viscous gel could be filtered through #1 filter paper
**weight of catalyst vs weight of chitosan

Example 19

A viscous solution was prepared by dissolving 10.0 g of chitosan with deacetylation degree of 90% in 225 ml of 20% acetic acid solution. 1.0 g of 18-crown-6 was added, followed by 28.6 g of acetic anhydride. The resulting mixture was stirred at room temperature for approximately eighteen hours. The reaction mixture was transferred into an addition funnel and 1600 ml of acetone was added dropwise with good agitation. The precipitate was collected and washed with acetone until no detectable amount of acetic acid was left. The resulting solid weighed 11.84 g. The degree of deacetylation (DD) value and O-acetylation value were determined by the $^1$HNMR method referenced in Example 8.

Example 20

Proceeding in a manner similar to that described in example 19, 10.0 g of chitosan, 225 ml of 20% acetic acid, 1.0 g of cis-dicylohexano-18-crown-6 and 28.6 g of acetic anhydride were combined to get 12.92 g of solid. The degree of deacetylation (DD) value and O-acetylation value were determined by the $^1$HNMR method referenced in Example 8.

Example 21

Following the procedure described in example 19, 10.0 g of chitosan, 225 ml of 20% acetic acid, 1.0 g of 15-crown-5 and 28.6 g of acetic anhydride were combined to get 12.52 g of solid. The degree of deacetylation (DD) value and O-acetylation value were determined by the $^1$HNMR method referenced in Example 8.

Example 22

Proceeding in a manner similar to that described in example 19, 10.0 g of chitosan, 225 ml of 20% acetic acid, 1.0 g of dibenzy-18-crown-6 and 18.6 g of acetic anhydride were reacted at room temperature for approximately eighteen hours. After the reaction, the mixture was quenched slowly into 1500 ml of isopropanol. The precipitate was collected and washed with isopropanol until no detectable amount of acetic acid remained. The resulting solid weighed 12.52 g. The degree of deacetylation (DD) value and O-acetylation value were determined by the $^1$HNMR method referenced in Example 8.

TABLE 10

Effect of crown ethers on the water solubility of randomly substituted partial N-, partial O-acetylated chitosan

| Samples | Catalyst | DD value (%) (by NMR) | O-acetylation (%) (by NMR) | Solubility in water (%) |
|---|---|---|---|---|
| Vanson chitosan | | 84 | 0 | 0.025 |
| Compare sample A | None | 63.5 | 16.9 | 0* |
| Compare sample B | None | 66.7 | 12.3 | 0.10# |
| Compare sample C | None | 55.6 | 21.3 | 0.015# |
| Example 19 | 18-crown-6(1:10)** | 47.4 | 55.1 | 1.87 |
| Example 20 | DC-18-crown-6(1:10) | 48.6 | 41.3 | 2.0 |
| Example 21 | 15-crown-5(1:10) | 51.3 | 47.5 | 1.70 |
| Example 22 | DB-18-crown-6(1:10) | 53.6 | 30.6 | 1.79 |

*The highly viscous gel could not be filtered through #1 filter paper
Only small amount of highly viscous gel could be filtered through #1 filter paper
**weight of catalyst vs. weight of chitosan DC-18-crown-6=Cis-dicyclohexano-18-crown-6

DB-18-crown-6=dibenzo-18-crown-6

Example 23

Following the procedure described in example 22, 10.0 g of chitosan, 225 ml of 20% acetic acid, 1.0 g of cetylpyridinium bromide monohydrate and 28.6 g of acetic anhydride were combined to get 11.56 g of solid. The degree of deacetylation (DD) value and O-acetylation value were determined by the $^1$HNMR method referenced in Example 8.

Example 24

Proceeding in a manner similar to that described in example 19, 10.0 g of chitosan, 225 ml of 20% acetic acid, 1.0 g of 1-dodecylpyridinium chloride monohydrate and 28.6 g of acetic anhydride were combined to get 12.992 g of solid. The degree of deacetylation (DD) value and O-acetylation value were determined by the $^1$HNMR method referenced in Example 8.

Example 25

Following the procedure described in example 19, 10.0 g of chitosan, 225 ml of 20% acetic acid, 1.0 g of 1-benzyl-3-hydroxy pyridinium chloride and 28.6 g of acetic anhydride were interacted to get 11.43 g of solid. The degree of deacetylation (DD) value and O-acetylation value were determined by the $^1$HNMR method referenced in example 8.

TABLE 11

Effect of pyridinium salts on the water solubility of randomly substituted partial N-, partial O-acetylated chitosan

| Samples | Catalyst | DD value (%) (by NMR) | O-acetylation (%) (by NMR) | Solubility in water (%) |
|---|---|---|---|---|
| Vanson chitosan | | 84 | 0 | 0.025 |
| Compare sample A | None | 63.5 | 16.9 | 0* |

TABLE 11-continued

Effect of pyridinium salts on the water solubility of randomly substituted partial N-, partial O-acetylated chitosan

| Samples | Catalyst | DD value (%) (by NMR) | O-acetyla-tion (%) (by NMR) | Solubility in water (%) |
|---|---|---|---|---|
| Compare sample B | None | 66.7 | 12.3 | 0.10# |
| Compare sample C | None | 55.6 | 21.3 | 0.015# |
| Example 23 | CPB (1:10)** | 50.9 | 22.6 | 2.0 |
| Example 24 | DPCl (1:10) | 48.1 | 57.5 | 2.0 |
| Example 25 | BHPCl (1:10) | 50.4 | 30.8 | 2.0 |

*The highly viscous gel could not filter through #1 filter paper
Only a small amount of highly viscous gel could be filtered through #1 filter paper
**weight of catalyst vs. weight of chitosan CPB=1-cetylpyridinium bromide, monohydrate DPCl=1-dodecylpyridinium chloride, monohydrate BHPCl=1-benzyl-3-hydroxy pyridinium chloride Example 26

In a procedure similar to that described in Example 8, 4.5 g of chitosan, 400 ml of 10% acetic acid, 1.0 g of tetrabutylammonium bromide and 9.0 ml of acetic anhydride were reacted at room temperature for approximately eighteen hours to get 5.6 g of solid. The degree of deacetylation (DD) value was 75.9% and O-acetylation value was 12.3% determined by $^1$H NMR method referenced in Example 8. The solubility in water was 1.86%.

Example 27

A mixture of 1.5 g of O-acetylated chitosan described in Example 26, 1.0 g of potassium hydroxide and 200 ml of methanol was stirred at room temperature for 18 hours. The resulting product was filtered and washed with 2×100 ml of isopropyl alcohol. The dried solid weighed 1.12 g. The degree of deacetylation (DD), value was 76.2% and O-acetylation value was 1.2% determined by the $^1$HNMR method referenced in Example 8. The solubility in water was 2.0%.

Example 28

Example 28 was prepared by following the procedure described in Example 8, by reacting 5.0 g of chitosan, with a deacetylation degree of 86%, 405 ml of 5% acetic acid, 0.34 g of tetrabutylammonium bromide and 8.4 ml of acetic anhydride to get 5.63 g of solid. The degree of deacetylation value (DD) was 64.7% and the O-acetylation value was 2.5% determined by the $^1$HNMR method referenced in Example 8. The solubility in water was 2.0%.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical preserving composition comprising:
   (a) at least one chitosan or chitosan derivative selected from randomly substituted water soluble, partial N-, partial O-acetylated chitosan and glycol chitosan in an amount from about 500 to 1000 ppm;
   (b) at least one buffer solution selected from among a borate buffer and a phosphate buffer; and
   (c) at least one biocidal adjuvant selected from disodium ethylenediaminetetraacetic acid (EDTA), nitriloacetic acid, or ethyleneglycol-bis(β-amino-ethylether)-N,N,N',N'-tetraacetic acid in an amount from about 150 to 500 ppm;
   wherein components (a), (b), and (c) are present in an amount such that the bacteria *Staphylococcus aureus*, *Pseudomonas aeruginosa*, and *Escherichia coli* are reduced by at least 99.9% (3 logs) within 14 days following a 0 day challenge date and 14 days following a 14 day re-challenge date; and
   the growth of *Aspergillus niger* and *Candida albicans* is inhibited within 14 days following a 0 day challenge date and 14 days following a 14 day re-challenge date.

2. The composition of claim 1, wherein the pH of the composition is from 6 to 8.

3. The composition of claim 1, further comprising at least one surfactant.

4. A contact lens solution comprising the composition of claim 1.

5. The composition of claim 1, wherein the chitosan or derivative thereof has a water solubility of at least 2.0%.

6. The composition of claim 1, wherein the composition comprises a borate buffer that comprises at least one of boric acid, sodium borate, potassium tetraborate, potassium metaborate, or mixtures thereof and the *Escherichia coli* is reduced by 4 logs or greater (99.99%) within 14 days following a 0 day challenge date.

7. The composition of claim 1, wherein the composition comprises a phosphate buffer that comprises at least one of sodium dihydrogen phosphate, disodium hydrogen phosphate, or mixtures thereof.

8. The composition of claim 1, further comprising at least one tonicity agent selected from sodium chloride, potassium chloride, or glycerol.

9. The composition of claim 1, further comprising as a surfactant a block copolymer of ethylene oxide and propylene oxide and the *Escherichia coli* is reduced by greater than 99.999% (5 logs) within 14 days following a 0 day challenge date.

10. The composition of claim 1, further comprising at least one viscosity control agent selected from polymeric saccharides, dextran cellulose derivatives, carboxymethyl cellulose, hydroxypropyl methylcellulose, polyvinyl alcohol, polyvinylpyrrolidinone, polyethylene glycol, or glycerin.

11. The composition of claim 1, wherein the composition has a pH of about 6 to about 8.

12. The composition of claim 1, wherein the composition has a pH of about 6.6 to about 7.8.

13. The composition of claim 1, wherein the composition has a pH of about 6.8 to about 7.2.

14. The composition of claim 1, wherein the chitosan or chitosan derivative has a weight average molecular weight ranging from about 5,000 to about 3,000,000.

15. The composition of claim 1, wherein the chitosan or chitosan derivative is a randomly substituted water soluble, partial N-, partial O-acetylated chitosan.

16. The composition of claim 15, wherein the randomly substituted water soluble, partial N-, partial O-acetylated chitosan has a degree of N-acetylation that ranges from about 47.4 to about 67.2.

17. The composition of claim 15, wherein the randomly substituted water soluble, partial N-, partial O-acetylated chitosan has a degree of O-acetylation that ranges from about 16.8 to about 57.5.

* * * * *